United States Patent [19]

Perten

[11] Patent Number: 4,479,055
[45] Date of Patent: Oct. 23, 1984

[54] INFRARED ANALYZER, ESPECIALLY FOR FOODSTUFFS SUCH AS FLOUR

[76] Inventor: Peter Perten, An der Barsbek 33 B, D-2000 Barsbeuttel, Fed. Rep. of Germany

[21] Appl. No.: 357,151

[22] Filed: Mar. 11, 1982

[30] Foreign Application Priority Data

Mar. 16, 1981 [SE] Sweden ................... 8101655

[51] Int. Cl.³ .................... G01N 21/35; G01N 21/11
[52] U.S. Cl. .................... 250/338; 250/343; 250/347
[58] Field of Search ............... 250/343, 347, 349, 353, 250/228, 358.1, 434, 432, 338; 356/418; 73/169; 141/71

[56] References Cited

U.S. PATENT DOCUMENTS

| | | | |
|---|---|---|---|
| 3,328,587 | 6/1967 | Brown et al. | 250/204 |
| 3,776,642 | 12/1973 | Anson et al. | 356/418 |
| 4,040,747 | 8/1977 | Webster | 356/418 |
| 4,082,464 | 4/1978 | Johnson, Jr. | 356/418 |
| 4,236,076 | 11/1980 | Judge et al. | 250/347 |
| 4,404,642 | 9/1983 | Rosenthal | 364/571 |

FOREIGN PATENT DOCUMENTS 3002559 7/1981 Fed. Rep. of Germany ...... 250/372

*Primary Examiner*—Janice A. Howell
*Assistant Examiner*—Constantine Hannaher
*Attorney, Agent, or Firm*—Fleit, Jacobson, Cohn & Price

[57] ABSTRACT

An analyzer for relative (percent etc.) measurement of amounts of certain substances, especially protein, water and/or oil in powdered, pulp-like or other non-rigid foodstuffs, is made to alternatingly irradiate a sample and a reference with collimated monochromatic IR-light. Both the sample and the reference are irradiated several times with light of various wavelengths in sequence. Photocells in an open spherical chamber, a so-called Ulbricht ball, receive from the sample and from the reference reflected diffuse light and convert it to electrical signals. In the beam path there is a window which allows said wavelengths to pass and which is in direct contact with the sample, which is thus not provided with a casing or own covering glass or the like. The sample is placed in a sample holder, which is formed by the window, possibly with a wall portion around said window, and a wall directly opposite to the window. The sample holder is completely closed when used but has an opening at one edge and a fixed or spring-biased bottom on the opposite edge. Between the wall and the window there is thus a space for filling with the sample through the opening in a direction transverse to the axis of the window. Said wall, and the frame of the analyzer itself with the window, can be separated from each other, so that said space is completely opened, and can be "flour-tight"0 sealed against each other. The analyzer can thus be used in such a position that the light beam is horizontal and strikes a vertical surface on the sample at a right angle.

9 Claims, 6 Drawing Figures

U.S. Patent
Oct. 23, 1984
4,479,055
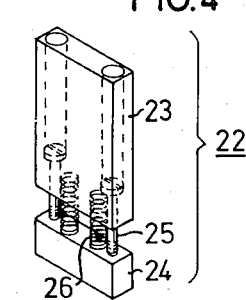
FIG.4
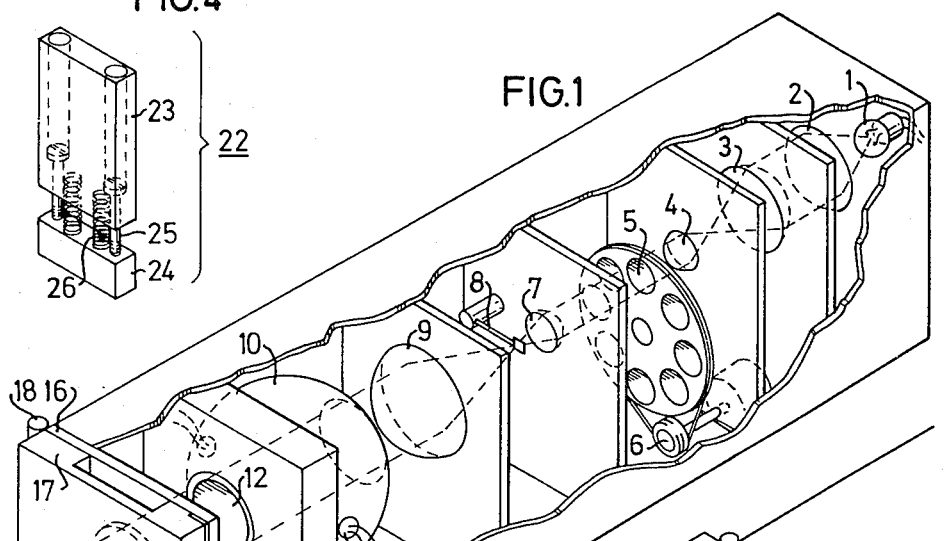
FIG.1
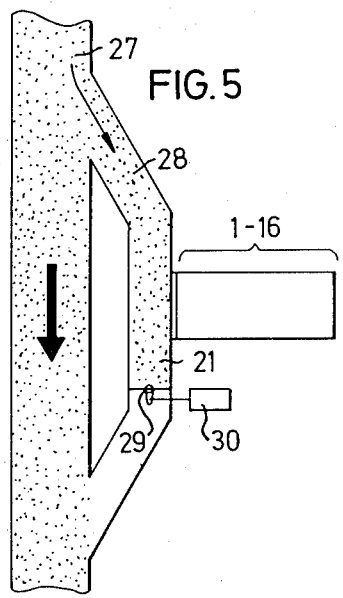
FIG.5
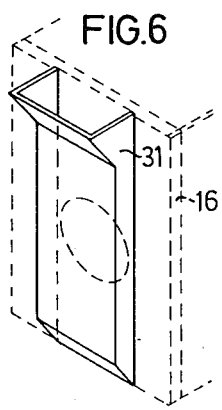
FIG.3
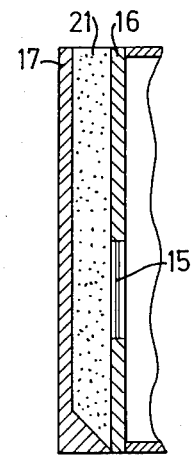
FIG.6
FIG.2

INFRARED ANALYZER, ESPECIALLY FOR FOODSTUFFS SUCH AS FLOUR

The invention relates to an infrared analyzer according to the preamble of the main claim. Such analyzers have been used for many years for material analyses, especially for investigating the presence of or the relative (in percent) amount of certain substances such as water, protein and oil in foodstuffs. The sample is irradiated with infrared light, usually in sequence with various wave lengths, and the light reflected by the sample is compared with the light reflected by a reference. High precision is required in the irradiation and the measurement of the reflected light. Among other things, the beam path between the sample itself and the photocell device must not be disturbed by substances affecting the infrared light, and if several windows of glass or the like are arranged in said portion of the beam path, they must be matched to each other. Furthermore, reflecting surfaces, such as glass surfaces, must be avoided as far as possible in this portion of the beam path, especially if the light passing to and from the reference does not pass through the same surfaces as the sample light. But even if it does pass through the same surfaces, they result in an undesirable repeated reflection even if they are treated to reduce reflection. And to this one can add the very common case where the sample does not consist of a solid rigid body or solid heavy particles but of flour or another fine powder, sticky granules algae or a fixed pulp such as chopped meat or sausage filling. For the reasons mentioned above, such samples should, on the one hand, not be covered by a casing, glass or the like and must, on the other hand, for known reasons be compressed with a certain pressure at least before they are placed in the analyzer for examination, but preferably even during the ongoing analysis. It is thus usual to place the sample in an open ball or similar box and to press it together before it is placed in the analyzer, and the means used for compacting must be removed before analysis. This usually has the result that the surface of the sample or possibly the entire sample will be uneven and that the sample can expand again before it is subjected to analysis, possibly partly because of the movement required to place the box with the sample in place in the analyzer. If the compacting is done with a glass sheet, it is often allowed to remain in place, but it makes the analysis both more difficult and less precise.

A typical sample box with a glass disc for resilient compacting is shown in U.S. Pat. No. 4,040,747 FIG. 2 and in addition to having some of the disadvantages mentioned, it is also complicated and difficult to clean. Therefore simple open balls are sometimes used, in which the sample must therefore be irradiated from above, at least if it consists of powdered, viscous, particulate or liquid substances and the like, since otherwise the analysis would be impossible or unreliable. Therefore this method is used in practice usually only for grain, apples and the like. A typical example of this is shown in i.e., U.S. Pat. No. 3,776,642, FIGS. 2, 14 and 15.

Some of the abovementioned disadvantages can also have indirect consequences. For example, it may be necessary to irradiate the sample vertically, requiring a so-called standing analyzer or redirecting the beam path by means of a mirror or prism. Another problem is that photocells during analysis in progress must not be able to be reached by other light than the infrared measuring light which must be and remain well collimated. Even when analysis is not in progress, the photocells must not be able to be reached by an appreciable ultraviolet light from daylight, fluorescent lights or another light source, because the as yet most suitable lead sulphide photocells at least are adversely affected by ultraviolet light.

The invention according to the main claim, especially in combination with one or more of the subclaims, makes it possible to avoid the abovementioned disadvantages, as well as making it possible to use simpler means for signal evaluation without sacrificing precision. It is also possible to use an analyzer according to the invention regardless of the angle between the irradiated surface of the sample and the vertical line for repeated or continued analysis of a flowing material (sample), to be examined. Examples of the invention are described below with reference to the accompanying drawing.

FIG. 1 shows schematically an analyzer.

FIG. 2 is a longitudinal section through the sample holder.

FIG. 3 shows an example of the portion of the analyzer for holding the sample.

FIG. 4 shows a sample compacter.

FIG. 5 shows a portion of a tube system provided with an analyzer, for a continuously flowing substance to be examined.

FIG. 6 shows a variation of the sample holder.

It should be observed that in the following for the sake of simplicity the word "flour" is used for all types of substances which are to be examined and are neither rigid as a whole nor consist of large solid grains. The term "glass" is used for solid substances which are permeable to infrared light. The abbreviations IR and UV refer to "infrared" and "ultraviolet" light, respectively.

FIG. 1 shows an IR analyzer according to the invention. A light source 1, for example an ordinary incandescent lamp or halogen lamp, xenon lamp or fluorescent lamp emits light via an optical system consisting of two biconvex lenses 2 and 3 to a condenser lens 4 and a light filter disc 5. This disc contains a plurality of optical monochromatic filters, each of which allows an individual IR wave length to pass. The disc 5 is rotated in steps by means of an electric step motor for example at 6 one complete revolution per 5-15 seconds. At each pause between the steps of rotation, only one of the filters in the disc is in the beam path. After this disc, the light is focused by a lens or composite optical system 7. At the focal point there is a light chopper in the form of a piezoelectrically or a magnetically driven flag 8 which periodically blocks the light at a higher frequency than 100 Hz, suitably 200 Hz, so that electric signals produced by the light will have this frequency to be easily amplified. The chopped light continues through a collimating condenser 9 into a chamber 10, which is here a hollow so-called Ulbricht ball with an opening facing the condenser 9 for incoming light. The condenser 9 produces a light beam of greater area than that at the filter. Directly opposite this opening, the ball 10 is provided with a corresponding, at least equally large window 15 for the light. This window can be optically closed by means of a disc 12 swingable in its own plane, which by means of an electromagnet 13 or a mechanical or electrical coupling to the filter disc 5, is swung synchronously therewith between a position completely blocking the light and a position completely freeing the window. An electromagnet 13 is shown schematically here for removing the disc 12 from the window, i.e. for freeing the light, with a spring 14 for returning the disc to the light-blocking position when the magnet 13 is currentless. The surface of the disc facing the interior of the ball can be flat or spherically arched but with approximately the same radius as the inside of the ball and constituting the reference mentioned below. This surface and the inside of the ball are suitably mat gilded to be reflecting and chemically resistant. The reference surface of the disc 12, can however consist of a durable substance other than that of the inside of the ball 10, for example polytetrafluorethylene.

When the disc 12 is swung away, the light passes to and through a glass window 15 to a sample 21 (FIG. 2) in a holder for the sample, and the window can be said to be a part of the sample holder, which otherwise consists of a portion 16 which is securely joined to the window and the analyzer frame, but which possibly can be removed, e.g. unscrewed, and a movable wall 17 which is easily affixed and easily removable, or can be swung or slid away from the portion 16, preferably without the use of any tool. For this purpose the portions 16 and 17 can be joined to each other by means of hinges 18 as according to FIGS. 1 and 3 or by means of snap locks, clamping means, magnets, hooks or other known means. The surface of the window 15 facing the sample should be planar with the wall portion of part 16 surrounding the window.

FIG. 2 is a vertical section through the sample holder in the plane of the beam path.

FIG. 3 shows the sample holder equipped with the hinge 18 between the fixed portion 16 and the movable wall 17, in the open position. FIG. 1 shows the same components in the closed position. The movable wall is ferromagnetic or contains a ferromagnetic member. When swung against the part 16, the wall 17 is held in place by a permanent magnet 19 in the portion 16. This arrangement can of course be reversed so that the portion 16 is completely or partially ferromagnetic and cooperates with a permanent magnet in the wall 17. There is also a heavy relay contact 20, which breaks the current to the light source 1 and/or controls the current to the electromagnet for the reference disc 12 in such a manner that said magnet is inoperative when the sample holder is opened by swinging away the wall 17, so that the reference disc 12 prevents external light from penetrating into the ball 10 and reaching the photocells 11 therein, since these can be adversely affected by penetrating daylight and other light containing UV. The contact 20 can also be coupled so that when the holder is open it also breaks the current to the step motor 6. Other means, e.g. signal means, can be controlled by the contact 20. The breaking of the current to the light source has the purpose, among other things, of keeping the photocells in darkness and preventing unnecessary generation of heat.

It should be mentioned that the magnetic operation of the contact 20 can be effected in different ways, for example by completely or partially completing the magnetic circuit of the permanent magnet 19 when the sample holder is closed, so that the heavy relay contact 20 is actuated by weakening of the magnetic field affecting it. If the permanent magnet 19 is mounted in the movable wall 17, on the other hand, the heavy relay contact can be operated by increasing the magnetic field acting on the same when the wall 17 is placed in contact with the portion 16.

When the wall 17 is placed with its edge portions against the portion 16, the two portions 16 and 17 are in "flour-tight" contact with each other except at the top where there is an opening, which is the upper end of a space in the form of a box-shaped shaft, which can possibly have a tapered portion at the bottom in one or both of the vertical shaft planes. The interior corners of the shaft should be rounded somewhat to facilitate cleaning. The flour, i.e. the sample, is introduced through said upper opening in the shaft, suitably by means of a funnel fitted to the oblong area of the opening. The shaft should not contain projections and/or depressions which could impede even distribution of the flour in the shaft or cleaning of the shaft after use.

The flour is then compacted in the shaft with a certain recommended pressure by means of a compacter, e.g. the compacter 22 shown in FIG. 4, consisting essentially of two different sized block shaped members 23 and 24 with guide pins 25 movably connecting them and compression springs 26. The two parts 23 and 24 can have the same cross sectional shape as the upper opening of the sample holder 15–17, through which the holder can be filled with flour. When the sample holder is filled, the compacter 22 is inserted into the opening with the underside of part 24 first and is pressed downwards in said shaft until the two parts 23,24 (or stop surfaces on the same) come into contact with each other. The flour in the holder has then been compressed with the pressure determined by the springs 26 in the compressed position. Thus the pressure and the surface characteristics are determined of the flour in contact with the window 15. This pressure and surface characteristics are fairly important for reliable measurement, since otherwise different values for several samples from the same flour can be obtained, i.e. the accuracy of the analyzer could not be better than the greatest difference between the just mentioned different values obtained with the same flour.

It should be pointed out that the bottom surface of the otherwise approximately block shaped shaft can be inclined at approximately 30°–60° downwards towards part 16. It is in principle unimportant if only part 16 or only wall 17 or both have the shaft-forming (space-forming) cavity according to FIGS. 1–3. The bottom of the shaft, regardless of whether its upper surface is inclined or not, can consist of a spring gate which can be pressed out to let out a portion of the sample, if the sample (21 in FIG. 2) is compacted too hard. This can happen in manual use of the compacter 22 according to FIG. 4 if one continues to press the compacter down into the shaft after both of the parts 23 and 24 have already been pressed together. In principle the compacter need not be spring-loaded and compressible in itself, but can be a rigid body with the compression pressure being determined by the spring force of the spring-loaded bottom gate.

The analyzer is used and operates in the following manner. The shaft (space) of the sample holder between the elements 17 and 15–16 is filled with flour. The flour in the shaft, which is the sample, is compacted with the compacter 22 according to FIG. 4 in the manner already described so that it is in direct contact, under a certain pressure, with the window 15 which is the only glass between the sample and the photocells 11. Pressing a start button lights the light source 1, the stepmotor 6 turns the filter disc 5 to a position with one of its filters in the beam path, and the magnet 13 swings away the reference disc 12 from the light exit opening of the ball 10, so that monochromatic, collimated light strikes the sample. The light reflected by the sample reaches the interior of the ball 10, where it reaches the photocells 11 through diffusion by the mat gilded interior wall of the ball. The photocells then send a corresponding AC signal with a frequency of—in this example—200 Hz due to the vibrations of the light chopper 8. The electrical photosignal is amplified, filtered, rectified and transformed into a digital signal which is registered by a microprocessor.

With said filter still stationary in the same position, the current to the electromagnet 13 is shut off, so that the spring 14 swings the reference disc 12 to the position where it blocks off light to the sample 13 and with its mat gilded surface reflects reference light into the ball 10, where this light diffusely reaches the photocells 11, which now send an electric reference signal, which is also an AC signal and is further processed in, in principle, the same manner as for the sample signal. If desired, it is possible to arrange or control the analyzer so as to produce several sample signals alternating with reference signals each time a single filter of the filter disc 15 remains in a stationary position, before the disc 15 is turned one step further by the stepmotor to the next filters.

For each sample, the abovementioned process is repeated for each filter in sequence. The filter disc 5 in FIG. 1 has eight filters, but with varying types of samples and analyses, measurements do not need to be taken with all of the filters, of course.

It will now be assumed that sample and reference measurement is done twice for each of six filters, the first and the second measurement having the indices 1 and 2 respectively, followed by the number of the filter (from 1-6 for six filters). P designates the sample signal and R designates the reference signal.

A microprocessor coupled to the actual analyzer 1–8 computes the value:

$$k_0 + k_1 \log \frac{R_{11} + R_{21}}{P_{11} + P_{21}} + k_2 \log \frac{R_{12} + R_{22}}{P_{12} + P_{22}} \cdots$$

$$k_6 \log \frac{R_{16} + R_{26}}{P_{16} + P_{26}}$$

where $k_0 \ldots k_6$ are constants determined according to the least-square method. For example, $R_{12}$ is the first measurement (No. 1) with the second filter (No. 2). The value of the above mathematical expression is thus obtained by first taking the logarithm of the quotient between the sum of two reference signal amplitudes and the sum of two sample signal amplitudes. Computing a quotient is not actually absolutely necessary, since the logarithm of a quotient is equal to the logarithm of the numerator minus the logarithm of the denominator.

The value obtained from the above formula is a measure, in the example described here, of the relative protein content of the flour, if the sample is a flour sample, irradiated by six different IR-light wavelengths in sequence, determined by the six filters used and selected in a suitable manner for such protein analysis.

With an analyzer according to the invention, it is possible to achieve very high precision. It is known that uncompensated temperature drift markedly reduces the precision of analyzers and other measuring instruments. In an analyzer according to the invention, temperature drift is compensated for preferably, but not necessarily, by processing in the computer changes in the reference signal R in such a manner that a corresponding compensating change of the sample signal is achieved by regulating the amplifying factor depending on changes in the reference signal. The device can, if necessary, also be made insensitive to changes in light strength in the light source 1. If the temperature drift is compensated for in the manner just described, it is easy to avoid having the analyzer interchange so to speak the effects of the temperature changes and the light strength changes on the electrical reference signal.

FIG. 5 shows the use of an analyzer according to the invention for control (analysis) of flour or the like in a cross-sectionally closed flour feed duct 27, i.e. usually a round or square pipe, for example a chute. This pipe is provided with a bypass 28 through which a portion of the flour passes either almost continuously or only between IR-measurements. The bypass 28 contains a gate 29 or similar closing device which can be operated by an electrical mechanism 30. The window 15 of the analyzer, according to FIGS. 1-3, is mounted in the bypass 28 so that the inside of this pipe and the window surface facing the interior of the pipe lie in the same plane. The sample holder then consists of the bypass portion, in which the window is included, and of the gate 29. The bottom of the sample holder is the gate when it is closed. The filling opening of the sample holder is the interior cavity of the pipe 28 itself above the window portion. Compacting of the flour sample 21 prior to and during analysis can be accomplished by the weight of the flour above the window in the bypass, or by means of a special compacting device, which does not need to be described here. As in the case described above, the gate 29 can be a spring-mounted gate, which opens if the pressure on the flour sample exceeds the desired or required value.

It is also possible to eliminate the bypass 28 altogether and use a portion of the main pipe 27 as a sample holder, provided with the analyzer 1-16 and the gate 29 arranged in the same manner as in FIG. 5 in the bypass 28. If the pipe 27 is a chute, so that the flour is advanced downwards by means of its own weight, the pipe 27 can be provided with a curve at a certain distance above the gate 29 so that essentially the amount of flour between the curve and the level of the window acts to compress the flour sample 21 against the window 15. If the pipe 27 is sufficiently short above the gate, or is sufficiently inclined, i.e. not vertical, a curve or the like can possibly be left out. If the feeding in the pipe 27 is done forcibly at excessive pressure against the closed gate, if the pressure is static (i.e. not continually increasing after closing the gate), it is possible to provide the pipe with a widened portion next to and above the gate. If the pressure is generated dynamically, so that is increases with increasing resistance in the pipe, it is possible to arrange an open duct in or next to the gate or make the gate spring-loaded as an overpressure valve to reduce the pressure on the flour sample. A variety of other possibilities are also available.

Finally, FIG. 6 shows a sample holder for use of individual flour samples as is the case in FIGS. 1-3. The sample holder is however designed, especially with its funnel-shaped outer wall 31 (corresponding to the wall 17 in FIGS. 1-3), to be slidable approximately like a cassette in a projector or camera for photography on glass plates.

The analyzer described above can be manufactured less expensively and with higher precision and more universily used as regards consistency of the sample than analyzers available on the market for grain flour and foodstuffs of similar consistency which are to be analyzed for relative protein content and/or water content.

What I claim is:

1. Infrared analyzer for relative determination of amounts of certain substances in a sample, especially in foodstuffs such as flour, by alternately irradiating the sample and a reference with infrared light, said analyzer comprising:

a light source;

means for separating infrared light from said light source;

means for transmitting the infrared light to a sample container for reflection by the sample;

reference means for providing a reference standard reflectance;

means for alternately receiving light reflected from the sample and from said reference means and converting the reflected light to electrical signals;

a container for the sample, said container including a light transmitting window and a first wall portion around the window, a second wall portion spaced from and movable relative to said first wall portion to define a suitable space for the sample between the window and said second wall, said container having an opening for receiving the sample in such a position that the sample can only be inserted into the space approximately parallel to the plane of the window.

2. Analyzer according to claim 1, wherein said opening for receiving the sample has the shape of a slot which has essentially the same area and shape as the cross section of said space, so that the sample can be easily introduced into the space.

3. Analyzer according to claim 1, wherein the window when the sample is irradiated is the only object which is struck by the light irradiating the sample.

4. Analyzer according to claim 1, wherein said space is sealed by a spring cover directly opposite said opening, so that samples introduced through the opening with excessive pressure against the cover open the cover and partially extrude out of the same.

5. Analyzer according to claim 1, including a compacter for compacting a sample introduced into said space, and that can be inserted into said opening and has a cross sectional area which corresponds substantially to the area of the opening and the space, wherein the compacter is made up of two relatively displaceably joined members, which can be resiliently pressed together so that the sample is compacted with spring force when the compacter is inserted into the space filled with the sample.

6. Analyzer according to claim 1, wherein said reference comprises a reference means having a surface facing away from the window and having the desired referential reflective properties, said means movable into and out of the light beam path to the window, so that said reference can be selectively positioned in the beam path completely screening off the window and the sample against irradiation.

7. Analyzer according to claim 1, wherein a window and a wall portion around the same are part of a conveyor tube for conveying sample material, and that a second, spaced wall is the portion of the conveyor tube not containing the window, which is located opposite the window so that said space is defined by a portion of the interior of the tube, and that said tube can be placed in contact with the window of the analyzer by moving the analyzer into abutment against a hole in the conveyor tube corresponding to the window and its surrounding wall portion so that said space is formed between the second wall and the window.

8. Analyzer according to claim 7, wherein the conveyor tube contains, downstream of the window with respect to sample feed, an openable and closable throttle, which in the closed position stops the advance of the sample.

9. Infrared analyzer for relative determination of amounts of certain substances in a sample, especially in foodstuffs such as flour, by alternately irradiating the sample and a reference with infrared light, said analyzer comprising:

a light source;

means for separating infrared light from said light source;

means for transmitting the infrared light to a sample container for reflection by the sample;

reference means for providing a reference standard reflectance;

means for alternately receiving light reflected from the sample and from said reference means and converting the reflected light to electrical signals;

a container for the sample, said container including a light transmitting window and a first wall portion around the window, a second wall portion spaced from said first wall portion to define a suitable space for the sample between the window and said second wall, said container having an opening for receiving the sample in such a position that the sample can only be inserted into the space approximately parallel to the plane of the window; and a compacter for compacting a sample introduced into said space, and that can be inserted into said opening and has a cross sectional area which corresponds substantially to the area of the opening and the space, wherein the compacter is made up of two relatively displaceably joined members, which can be resiliently pressed together so that the sample is compacted with spring force when the compacter is inserted into the space filled with the sample.

* * * * *